(12) United States Patent
Grolman et al.

(10) Patent No.: US 10,029,977 B2
(45) Date of Patent: Jul. 24, 2018

(54) PROCESS FOR PREPARING A DIAMINE/DICARBOXYLIC ACID SALT

(71) Applicant: DSM IP ASSETS B.V., Heerlen (NL)

(72) Inventors: Eric Grolman, Echt (NL); Rudy Rulkens, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/258,835

(22) Filed: Sep. 7, 2016

(65) Prior Publication Data

US 2016/0376220 A1  Dec. 29, 2016

Related U.S. Application Data

(63) Continuation of application No. 14/234,248, filed as application No. PCT/EP2012/064698 on Jul. 26, 2012, now Pat. No. 9,475,753.

(30) Foreign Application Priority Data

Jul. 26, 2011 (EP) .................................. 11175378

(51) Int. Cl.
| | | |
|---|---|---|
| *C07C 209/68* | (2006.01) | |
| *C07C 211/09* | (2006.01) | |
| *C07C 211/12* | (2006.01) | |
| *C07C 51/41* | (2006.01) | |
| *C07C 55/14* | (2006.01) | |
| *C07C 55/20* | (2006.01) | |
| *C07C 63/28* | (2006.01) | |
| *C08G 69/04* | (2006.01) | |
| *C08G 69/26* | (2006.01) | |

(52) U.S. Cl.
CPC .......... *C07C 209/68* (2013.01); *C07C 51/412* (2013.01); *C07C 55/14* (2013.01); *C07C 55/20* (2013.01); *C07C 63/28* (2013.01); *C07C 211/09* (2013.01); *C07C 211/12* (2013.01); *C08G 69/04* (2013.01); *C08G 69/265* (2013.01); *C07B 2200/13* (2013.01)

(58) Field of Classification Search
CPC ... C07C 209/68; C07C 211/09; C07C 211/12; C07C 51/412; C07C 55/14; C07C 55/20; C07C 63/28; C08G 69/04; C08G 69/265; C07B 2200/13

See application file for complete search history.

(56) References Cited

U.S. PATENT DOCUMENTS

| | | | |
|---|---|---|---|
| 3,904,677 A | 9/1975 | Campbell | |
| 4,131,712 A * | 12/1978 | Sprauer | C08G 69/28 528/335 |
| 5,801,278 A | 9/1998 | Bletsos et al. | |
| 2013/0018166 A1 | 1/2013 | Nakai et al. | |
| 2013/0172521 A1 | 7/2013 | Nakai et al. | |

FOREIGN PATENT DOCUMENTS

| | | |
|---|---|---|
| EP | 2 554 566 | 2/2013 |
| EP | 2 644 638 | 10/2013 |
| FR | 2207901 | * 6/1974 |

OTHER PUBLICATIONS

English Translation of FR2207901, Jun. 21, 1974, pp. 1-10.*
International Search Report for PCT/EP2012/064698 dated Nov. 7, 2012.
EP Appln. 12740151.1, Communication pursuant to Rule 114(2) EPC (Apr. 1, 2016).

* cited by examiner

*Primary Examiner* — Pancham Bakshi
*Assistant Examiner* — Mark R Luderer
(74) *Attorney, Agent, or Firm* — Nixon & Vanderhye P.C.

(57) ABSTRACT

The present invention also relates to a process for preparing a diamine/dicarboxylic acid salt wherein the dicarboxylic acid comprises an aromatic dicarboxylic acid and is provided in a powder form; the diamine is provided in a liquid form gradually dosed to the dicarboxylic acid powder, while keeping the dicarboxylic acid powder in constant movement; the processing temperature is above 0° C. and below the boiling temperature of the diamine and the melting temperature of the acid and the salt, and the reaction mixture comprises at most 5 wt. % of water. The present invention also relates to an anhydrous diamine/dicarboxylic acid salt obtainable by the process according to invention, or any embodiment thereof as described above.

25 Claims, 13 Drawing Sheets

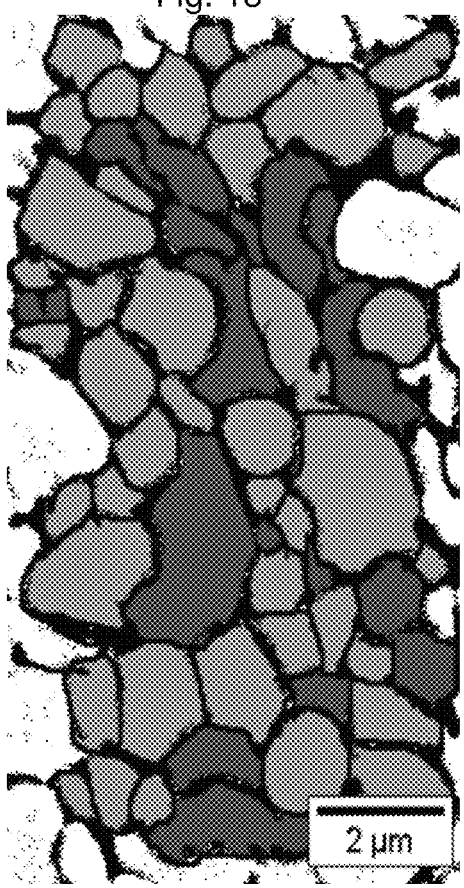

PROCESS FOR PREPARING A DIAMINE/DICARBOXYLIC ACID SALT

This application is a continuation of U.S. application Ser. No. 14/234,248, filed Apr. 18, 2014 (now U.S. Pat. No. 9,475,753), which is the national phase application of international application PCT/EP2012/064698, filed Jul. 26, 2012, which designated the US and claims priority to European Application No. 11175378.6, filed Jul. 26, 2011, the entire contents of each of which are hereby incorporated by reference.

The present invention relates to a process for preparing a diamine/dicarboxylic acid salt comprising contacting a diamine with a dicarboxylic acid to provide a reaction mixture in which said diamine and said dicarboxylic acid react to form a diamine/dicarboxylic acid salt.

Diamine/dicarboxylic acid salts are widely used as starting materials for the production of polyamides. Particularly favourable, the diamine/dicarboxylic acid salt has a solid particulate form.

Poly(hexamethylene adipamide) (nylon 6,6) polymer is typically manufactured commercially by first making an aqueous salt solution from its monomers hexamethylene diamine and adipic acid. The diamine is supplied as a dilute aqueous solution so that the resulting hexamethylene diammonium adipate (6,6 salt, often referred to as nylon 6,6 salt) solution usually contains about 50 wt. % water. This solution is then used as a starting material and initial reaction medium for the solution/melt polymerization of nylon 6,6. Sometimes also aqueous solutions of nylon 6,6 salt are sold commercially, which are typically transported as warm solutions of about 50 wt. %. Storing times are limited due to the unwanted polymerization and warm storage of the solutions is required to avoid precipitation of the sold in the storage vessel. Nylon 6,6 salt is also commercially available as a solid. Techniques are known for precipitating the salt from the solution such as by adding a non-solvent for the salt to the solution, e.g., isopropanol. Such processes require the subsequent recovery of the non-solvent from the solution. The salt can be recovered as a stable, free-flowing powder which is easily shipped for use at remote locations. This is less dangerous than shipping caustic volatile hazardous aqueous solutions of hexamethylene diamine, which solution is a typical form for shipping the diamine to keep it in the liquid state at moderate temperatures.

An alternative process to produce diamine/dicarboxylic acid salts in substantially solid particulate form is known from U.S. Pat. No. 5,801,278. In the process from U.S. Pat. No. 5,801,278 the reaction of the diamine with a dicarboxylic acid is carried out in the presence of about 0.5 to about 25 wt. % water, preferably 2-10 wt. % water, based on the weight of the reaction mixture, while providing conditions in the reaction mixture such that the reaction mixture is in substantially solid particulate form. These conditions were met by employing a temperature well below room temperature, more particularly using a cryogenic medium, such as dry ice or liquid nitrogen, in the reaction mixture. The reactants were mixed in a short time and subsequently kneaded for allowing the reactants to react. Where the reaction was performed without a cryogenic medium, it resulted in formation of a paste rather than a free flowing powder. Also the homogeneity of the resulting product was not good.

In U.S. Pat. No. 5,874,520 anhydrous nylon salts are made in a solid state process in which solid diamine carbamates are contacted and mixed with solid dicarboxylic acids. These compounds are in particular mixed under high shear conditions, which is to reveal "fresh" particle surfaces having unreacted molecules by frictional rubbing or the like. Cryogenic media (e.g. dry ice or nitrogen) are used, not only to control the heat of the reaction, but also to maintain the reaction in the solid state.

In U.S. Pat. No. 5,874,520 substantially anhydrous nylon salts are made in a solid state process in which solid diamine carbamates are contacted and mixed with solid dicarboxylic acids in a near instantaneous reaction to produce the salt under conditions of high shear. As mentioned in U.S. Pat. No. 5,874,520 the reaction can be continued by removing the salt formed at the particle-particle interface (such as by frictional rubbing or the like) to reveal "fresh" particle surfaces having unreacted molecules.

Use of an organic solvent or a cryogenic medium in the way as described above complicates the process and is often not desired or even prohibits large scale production. A special disadvantage of using cryogenic media is that they may allow moisture to be drawn from the ambient air, which in turn may decompose some of the carbamate salt, as mentioned in U.S. Pat. No. 5,874,520, but also may prevent the salt to be recovered from the process as a stable, free flowing powder. The use of chemicals like dry ice ($CO_2$) and/or nitrogen, which are subsequently emitted to the surrounding involves extra costs, and is environmentally unfavourable due to the carbon footprint of the nitrogen and $CO2$ used.

The aim of the invention is to provide a process for preparing a diamine/dicarboxylic acid salt, which eliminates the need for using an organic solvent or a cryogenic medium. The aim is further to provide a process wherein the diamine/dicarboxylic acid salt is produced in solid particulate from, preferably as a free flowing powder.

This aim has been achieved by the process according to the invention, comprising steps comprising contacting a diamine with a dicarboxylic acid to provide a reaction mixture in which said diamine and said dicarboxylic acid react to form a diamine/dicarboxylic acid salt, wherein:

(a) the dicarboxylic acid comprises an aromatic dicarboxylic acid;

(b) the dicarboxylic acid is provided in a powder form;

(c) the diamine is provided in a liquid form;

(d) the contacting is performed by gradually dosing diamine liquid to dicarboxylic acid powder, while keeping the dicarboxylic acid powder in constant movement;

(e) the reaction mixture is kept in constant movement for a time period directly following completion of the dosing, (f) (d) and (e) are carried out at a temperature above 0° C. and below all of the following: the boiling temperature of the diamine and the melting temperatures of the dicarboxylic acid, the diamine/dicarboxylic acid salt and any intermediate reaction product, and (g) in (d) and (e) the reaction mixture comprises at most 5 wt. % of water, relative to the total weight of the diamine and dicarboxylic acid.

The effect of the process according to the invention is that the salt is obtained in solid particulate form being substantially anhydrous. By "substantially anhydrous" is meant herein that the salt generally contains no more than 5 wt. % of water, relative to the total weight. The salt is recovered from the process is a stable, substantially free flowing powder. The salt is obtained as a generally homogenous product, suitable for use in common commercial processes for the manufacture of polyamide polymers. This result is achieved without a precipitation step involving using an organic solvent and without the use of a cryogenic medium in the reaction mixture. The process does not require high shear mixing, and the process can easily be scaled up to industrial scale.

The temperature at which (d) and (e) are carried out is herein also referred to as processing temperature. This temperature is measured in the reaction mixture.

With the term melting temperature (Tm) is herein understood the temperature, measured by the DSC method according to ISO-11357-3.2, 2009, in a nitrogen atmosphere with heating and cooling rate of 20° C./min. Herein Tm is the temperature at the peak of the melting peak in the first heating cycle.

With the term boiling temperature for the diamine is herein understood the boiling temperature measured at the prevailing pressure when dosing of the diamine. In a preferred embodiment (d) and (e) are carried out at a temperature below the boiling temperature of the diamine measured at the lowest pressure applied during the dosing of the diamine.

With the expression "gradually dosing" is herein understood that the diamine is dosed at sufficiently low amount per time unit as to not excessively wet the particles at any time to prevent sticking of the particles together, clogging and lump formation. This excludes the diamine to be dosed all at once or nearly so. However, it does not exclude the diamine to be dosed in reasonably short time, as it appeared that reaction of added diamine with the dicarboxylic acid is reasonably fast thus preventing the diamine to be accumulated in unreacted form. The reaction speed might depend on the type of diamine and dicarboxylic acid. The dosing regime suitable to be applied in, for example large scale operations for specific combinations of diamine and dicarboxylic acid can be established by routine measurements by simply varying the dosing speed, e.g. starting with a low dosing speed, and gradually increasing the speed.

The minimum duration of the time period directly following completion of the dosing, during which the reaction mixture is kept in constant movement is typically chosen to be at least sufficient to prevent sticking and agglomeration upon discharging from the reactor in which the process is carried out. This is affected by the various factors, such as dosing speed, reaction temperature and combination of specific diamines and dicarboxylic acids. Suitably, the time period is in the range starting from and including 10 minutes up to and including 1 hour. The time period may also be longer than 1 hour. Depending on processing conditions, in particular with a very slow dosing speed, in particular with a very slow dosing speed at the end of the dosing of the diamine, this time period can be much shorter, e.g. between 0 and 10 minutes.

The diamine and the dicarboxylic acid in the reaction mixture can be present in a molar ratio varying over a large range, with initially the carboxylic acid being present in large excess over the diamine. During the dosing of the diamine this excess diminishes and the molar amounts get closer to parity, while if further diamine is added the diamine might be in excess over the diacid. This is not a problem, since adding some excess of diamine still results in a stable solid particulate material.

However, a large deviation of the molar ratio from parity could be less desirable for further processing to produce polyamide polymers, as this would require supplementation of diamine in case of excess dicarboxylic acid, whereas in case of excess of diamine this would require supplementation of extra dicarboxylic acid and/or, with a larger excess of diamine, lead to excessive loss of volatile amines. Suitably the molar ratio of diamine over dicarboxylic acid (D/DA) is in the range of 0.9-1.1. Preferably the D/DA molar ratio is in the range of 0.95-1.05. In practice it is preferred that the diamine is at least at parity, thus with a D/DA of at least 1.0, or in a slight excess, such as with a D/DA molar ratio of about 1.005-1.02, corresponding to 0.5 to 2% molar excess of diamine. Therefore, more preferably, the D/DA ratio is in the range of in the range of 1.00-1.02. Even with such low excess, or even no excess at all, i.e with equimolar amine, the reaction goes to complete conversion or essentially so, i.e. a small amount of residual dicarboxylic acid if any is observed, e.g. with wide angle X-ray diffraction (XRD). Of course, with less than equimolar diamine, the presence of a certain amount of residual dicarboxylic acid cannot be excluded.

The diamine and the dicarboxylic acid used in the process according to the invention suitably consist of mixtures of different compounds, i.e. mixtures of different diamines and/or mixtures of different dicarboxylic acids. The mixtures can be chosen such as to provide for the preferred composition of the copolyamide polymer, depending on the required polymer properties.

In a particular embodiment, the dicarboxylic acid is a mixture of an aliphatic dicarboxylic acid and an aromatic dicarboxylic acid. This has the advantage that the salt not only is in a solid particulate form but also comprises a mixture of dicarboxylic acids as are used in several semi-aromatic polyamides produced on commercial scale.

It is noted that the use of the expression "a" or "an", as used herein, for example in here above "an aliphatic dicarboxylic acid" and "an aromatic dicarboxylic acid" is intended herein to include both singular as well as plural forms, unless expressly noted otherwise.

In general the aliphatic dicarboxylic acid and the aromatic dicarboxylic acid are suitably present in a molar ratio between 90:10 and 10:90, although depending on specific diamine and dicarboxylic acid components a ratio of 90:10 or above might be used while still obtaining a solid particulate material. Preferably the molar ratio is in the range of from 80:20 up to and including 20:80.

In a preferred embodiment, the mixture of aliphatic dicarboxylic acid and aromatic dicarboxylic acid is a dry blend of solid particles of the aliphatic dicarboxylic acid and solid particles of the aromatic dicarboxylic acid. It has been observed that though the dicarboxylic acids are not mixed on molecular scale prior to the salt production process, the salt is obtained in a solid particulate form, even when the corresponding salt of the aliphatic dicarboxylic acid, i.e. without the aromatic dicarboxylic acid, gives difficulties in or prohibits the formation of a solid particulate. The use of a dry blend prevents the need of any complex premixing step such as dissolving, mixing and precipitation steps.

In cases where a combination of different dicarboxylic acids are used, different salts can be formed which can be reflected in different melting peaks, in particular in case where the different dicarboxylic acids are used in the form of a dry blend. These melting temperatures shall all be considered when choosing the processing conditions. The processing temperature shall be kept below the melting temperature of each.

In a particular embodiment the aliphatic dicarboxylic acid and the aromatic dicarboxylic acid are present in a molar ratio between 10:90 and 50:50.

In another particular embodiment, the dicarboxylic acid essentially consists of aromatic dicarboxylic acid, with which is meant that the dicarboxylic acid more particularly consists of 90-100 mole % of aromatic dicarboxylic acid and 10-0 mole % of aliphatic dicarboxylic acid. Preferably dicarboxylic acid consists of 95-100 mole % aromatic dicarboxylic acid, respectively 5-0 mole % aliphatic dicarboxylic acid. The mole percentages (mole %) mentioned are relative to the total molar amount of aliphatic dicarboxylic acid and aromatic dicarboxylic acid.

The aromatic dicarboxylic acids not only favour the formation of the diamine/dicarboxylic acid salt as a solid particulate material, it also reacts readily with the diamine. The salts based on dicarboxylic acid essentially consisting of aromatic dicarboxylic acid are furthermore favourably used in the production of polyamides in combination with a salt based on aliphatic dicarboxylic acid. Herein the salt based on aliphatic dicarboxylic acid comprises or is, for example, nylon 6,6 salt, i.e. the salt of 1,6-hexane diamine and adipic acid. Nylon 6,6 salt is produced on very large scale and available worldwide. Combinations of these salts allow the production of polyamides with compositions varying over a wide spectrum, without the need to have a large inventory on different salts or mixing in of additional amines or acids.

Examples of suitable aromatic dicarboxylic acids include isophthalic acid, terephthalic acid, 2,6-naphthalene dicarboxylic acid and 4,4'-biphenyldicarboxylic acid, which can be used individually as well as in any combination thereof. Preferably, the aromatic dicarboxylic acid comprises 2,6-naphthalene dicarboxylic acid and/or terephthalic acid. More preferably the aromatic dicarboxylic acid comprises terephthalic acid in an amount of at least 25 mole %, better at least 50 mole %, still better at least 75 mole %, or even consists of terephthalic acid. Herein the mole % are relative to the total molar amount of aromatic dicarboxylic acid.

The aliphatic dicarboxylic acid in the process according to the invention may be a non-cyclic, either linear or branched dicarboxylic acid or a cyclic dicarboxylic acid. Suitably the aliphatic dicarboxylic acid is an aliphatic dicarboxylic acid having 4-18 carbon atoms, for example, 6, 8, 10 or 12 carbon atoms. Suitably the non-cyclic dicarboxylic acid is chosen from the group of 1,6-hexanedioic acid (also known as adipic acid), 1,8-octanedioic acid, 1,9-nonanedioic acid, 1,10-decanedioic acid (also known as sebacic acid), 1,11-undecanedioic acid, 1,12-dodecanedioic acid, 1,13-tridecanedioic acid, 1,14-tetradecanedioic acid, 1,15-pentadecanedioic acid, 1,16-hexadecanedioic acid, 1,17-heptadecanedioic acid and 1,18-octadecanedioic acid. A suitable cyclic aliphatic dicarboxylic acid is trans-1,4-cyclohexanedicarboxylic acid.

Preferably, the aliphatic dicarboxylic acid comprises adipic acid or sebacic acid. Adipic acid is most widely used in polyamides. Sebacic acid is available from renewable resources.

In addition, mono-acids, for example benzoic acid, can be added to the mixture of acids in any desired quantity, as required for quality of the polymer product eventually obtained. Usually around 0.5 to 3 mole % (relative to the acids already present) of mono-acids are used in polymerization processes to control the molecular weight of the resulting polyamide. Suitably, the amount of monocarboxylic acid, if used at all in the salt preparation process, is in the range of 0.01-5, preferably 0.1-3 mole %, relative to the total molar amount of dicarboxylic acid.

The diamine in the process according to the invention can be selected from those diamines suitable for use as starting materials for the manufacture of polyamides. These diamines include aliphatic diamines, alicyclic diamines, aromatic diamines and any mixture thereof. Suitable aromatic diamines are, for example, isophenylene diamine and paraphenylene diamine. Suitably, the aliphatic diamines are aliphatic diamines with 2-18 carbon atoms, which may be either linear or branched, or alicyclic. More preferably the aliphatic diamines have 2-12 carbon atoms per molecule, such as 1,2-ethylene diamine, 1,3-propylene diamine, 1,4-butane diamine, 1,5-pentane diamine, 1,6-hexane diamine, 1,8-octane diamine, 1,9-nonane diamine, 1,10-decane diamine, 1,11-undecane diamine, 1,12-dodecane diamine, 2-methyl-1,5-pentane diamine and 2-methyl-1,8-octane diamine. Examples of suitable alicyclic diamines are 1,4-trans-cyclohexane diamine and 1,4-trans-diaminomethylcyclohexane.

Preferred diamines are those most widely used in semi-aromatic polyamides produced on large scale, which include 1,4-butane diamine, 1,6-hexane diamine, and 1,9-nonane diamine.

In case of longer chain diamines, such as with C8-C18 diamines, the reaction is slower and longer dosing time and/or higher reaction temperatures are needed, compared to shorter chain diamines with 2-7 carbon atoms per molecule. Preferably, the C8-C18 diamines are combined with a C2-C7 diamine. The amount of the C2-C7 diamine can remain relatively low, which already having a significant effect on the reaction rate, thus allowing for a shorter dosing time and/or a higher reaction temperature. Suitably, the molar ratio between short chain diamine and long chain diamine is in the range of 1/99-25/75, more particular 2/98-20/80, or even 5/95-15/85. Of course also mixtures with a higher molar amount of short chain diamines are suitable for the salt preparation process Preferably, the short chain diamine is a C2-C6 diamine. More preferably, the diamine used in the process according to the invention comprises 1,4-butane diamine and/or 1,6-hexane diamine, more preferably 1,4-butane diamine.

As mentioned above the process is carried out at a temperature below the boiling temperature measured at the prevailing pressure when dosing of the diamine. Where the diamine used in the process of the invention is a mixture of at least two different diamines, the boiling temperature of the diamine (TbDiamine) below which the temperature in the process is to be kept, is the lowest of the boiling temperature of any of the at least two diamines and, in case it occurs, any azeotrope thereof. The boiling temperature, respectively the boiling temperatures referred to herein are each the boiling temperature measured at the prevailing pressure at which the contacting and reaction are carried out. The purpose thereof is to prevent evaporation of the diamine rather than the diamine contacting and reacting with the dicarboxylic acid.

In a preferred embodiment process steps (d) and (e) are carried out at a temperature below the boiling temperature of the diamine measured at the lowest pressure applied during the dosing of the diamine. In case of a mixture of at least two different diamines, the boiling point of the diamine is the lowest of the boiling temperature of any of the at least two diamines and, in case it occurs, any azeotrope thereof.

In the process according to the invention the diamine and dicarboxylic acid are contacted by gradually dosing the diamine liquid to the dicarboxylic acid powder, while keeping the dicarboxylic acid powder in constant movement. Preferably the diamine is dosed onto the dicarboxylic acid powder, such that it does not first get into contact with a part of a side wall of a reactor vessel in which the process is carried out. This in order to prevent sticking onto the side wall and lump formation of dicarboxylic acid powder and salt subsequently formed. Suitably the contacting is performed by spraying or dripping the diamine onto the moving dicarboxylic acid powder.

The process according to the invention can in principle be carried out in any type of reactor in which powder material can be kept in constant movement by mechanical agitation. By the mechanical agitation a mechanically agitated powder bed is formed. Suitable reactors for the process to be carried out in are, for example, a tumble mixer, a ploughshare mixer, a planetary screw mixer, also known as Nauta mixer, a conical mixer and a fluidized bed, for example a circulating fluidized bed reactor. The mixers may also contain a wall heating and/or cooling, as is typical for dryers. In said case the mixers may also be referred as dryer, as in tumble dryer conical dryer and planetary screw drier.

The said mixers are all low shear mixers. Further information on these and other low shear mixer apparatus can be found in the book "Handbook of Industrial Mixing—Science and Practice" edited by: Paul, Edward L.; Atiemo-Obeng, Victor A.; Kresta, Suzanne M. (Publisher: John Wiley & Sons; 2004; ISBN: 978-0-471-26919-9; Electronic ISBN: 978-1-60119-414-5), more particularly in Chapter 15, part 15.4 and 15.11.

The fact that the process according to the invention can be carried out without applying a high shear and still provide a high degree of conversion is highly surprising. In fact, the constant movement in step (d) and (e) of the process according to the invention can be accomplished with low shear agitation avoiding attrition of the dicarboxylic acid powder. With such low shear there is also no significant break-up of the salt particles, more particular, the d10 of the resulting diamine/dicarboxylic acid salt is at least the same as that of the starting dicarboxylic acid powder. In fact the attrition can be so low, or even absent at all, that the particle size distribution is hardly affected, apart from the fact that the size of the dicarboxylic acid powder particles might be even increased during the reaction with the diamine.

The advantage of such low shear agitation without attrition of the dicarboxylic acid powder, is that amount of fines produced during the process is low, and that problems of fouling, dusting, sagging upon storage, and reduced flowability due to clogging of fines is reduced.

In a preferred embodiment of the process according to invention, the dicarboxylic acid powder used therein comprises a low amount of particles with small particle size. Also preferred is a dicarboxylic acid powder having a narrow particle size distribution. The advantage thereof is that also the resulting diamine/dicarboxylic acid salt so produced also has less small particles, respectively a relative narrow particle size distribution, and optionally even better flow properties. Suitably, the use of dicarboxylic acid powder with low amount of small particles and/or narrow particle size distribution, is combined with low shear agitation.

Suitably, the dicarboxylic acid powder has a particle size distribution with a d10 of at least 15 μm and a d90 of at most 1000 μm. Suitably, the dicarboxylic acid powder also has a median particle size (d50) in the range of 40-500 μm. Herein the particle size distribution is measured with laser granulometry by the method according to ISO 13320 at 20° C.

Preferably the d10 for the particle size distribution of the dicarboxylic acid powder is in the range of 15-200 μm, more preferably in the range of 16-160 μm. Preferably, the d90 is in the range of 100-1000 μm, more preferably in the range of 150-800 μm. Preferably, the d50 is in the range of 40-400 μm, more preferably in the range of 40-400 μm. Also preferably the dicarboxylic acid powder has a particle size distribution with a Span, defined by the ratio of (d84-d16)/d50, of at most 5. The advantage is that also the resulting diamine/dicarboxylic acid salt has a narrower particle size distribution and the flow is further improved.

The reaction of the diamine and the dicarboxylic acid is carried out under conditions such that the reaction mixture is continuously in substantially solid particulate form, i.e. discrete particles exist throughout the duration of the addition of the diamine and the subsequent reaction time. The reaction of a diamine with a dicarboxylic acid is strongly exothermic, and local overheating could result in some minor agglomeration. Without any temperature control, the reaction mixture could, depending on the reactants used, form a paste and agglomerate into a single mass, rather than to remain in the substantially solid particulate form. However, by applying the process according to the invention, wherein the diamine is gradually dosed, and the reaction mixture is kept in constant movement during the diamine dosing and the further reaction, optionally supported by external temperature control measures, the temperature is easily controlled and local overheating is minimal if any.

The temperature control for maintaining substantially solid particulate form is suitably achieved when during the gradual addition of the diamine and mechanical agitation of the reaction mixture heat is transferred away from the reaction mixture, such as to keep the temperature of the reaction mixture, i.e. processing temperature, within the temperature range indicated above, i.e. in between 0° C. and either the boiling temperature of the diamine (TbDiamine), the melting temperature of said dicarboxylic acid, of the diamine/dicarboxylic acid salt and of intermediate reaction products in the reaction mixture, whichever is the lowest. This heat transfer is advantageously accomplished by employing a reactor equipped with a heat exchanger. The heat exchanger can be, for example, an internal heat exchanger, such as baffles with a cooling medium inside the baffles, and/or an external heat exchanger, such as a double wall reactor vessel, with a cooling medium inside the double wall.

The processing temperature suitably is chosen to be below the boiling temperature of water. Thus, the processing temperature may as well be chosen to be equal to or higher than the boiling temperature of water. If the processing temperature is equal to or higher than the boiling temperature of water under the prevailing conditions of the process, care has to be taken to either maintain the amount of water in the reaction mixture as low as possible, preferably below 1 wt. %, relative to the total weight of the reaction mixture, and/or to prevent the presence of cold spots where water vapour could condense and powder particles could stick to the wall. This latter can be achieved by using a reactor with a wall temperature above the boiling temperature of water. The processing temperature can still be kept below the upper limit by applying a sufficiently low dosing speed for the diamine. By applying a processing temperature above the boiling temperature of water, the diamine/dicarboxylic acid salt in solid particulate form is obtained with even lower water content. Special care might be paid to prevent diamine to be entrained and removed together with the water vapour.

Suitably, the diamine and the dicarboxylic acid are contacted at a temperature between 0° C. and the boiling temperature of water. Herein the boiling point is the boiling point as measured for the prevailing pressure at the time of dosing of the diamine. The process is optionally carried out under atmospheric conditions. The process and dosing may well be carried out at pressures above and/or below atmospheric pressure. Preferably a slight overpressure is applied, optionally operating in an inert atmosphere of nitrogen or argon, for example to avoid intake of air.

A particularly preferred way of carrying out the invention is to expose the dicarboxylic acid in powder form to a low ambient temperature, i.e., room temperature, and subsequently add a diamine, optionally containing up to about 2 percent water combined therewith, in liquid (molten) form. Using such amines, some heating might be required to maintain these amines in liquid form for ease of addition to the reaction mixture. Moreover, the rate of addition of the liquid diamine can be easily controlled to match the heat transfer conditions, i.e., the liquid addition can be adjusted to a sufficiently low rate to prevent the formation of a paste.

Unlike conventional diamine/dicarboxylic acid salt formation processes which are carried out in aqueous solutions containing approximately 50 wt. % water, the water content of the reaction mixture in the process of the invention is at a much lower level, that is, at most 5 wt. %, preferably at most 1 wt. % relative to the weight of the reaction mixture. The water content may be even below 0.5 wt. %. Despite the low water content, the salt formation reaction occurs to sufficient extent to favour the formation of the salt in sufficiently short time and with reasonable to good homogeneity. With the water content kept within the said limits, the diamine/dicarboxylic acid salts are recovered as a free-flowing powder, or substantially so, which facilitate subsequent handling.

The diamine/dicarboxylic acid salts, which can be stored and shipped in substantially solid particulate form, are useful starting materials for the manufacture of polyamide polymers. The salts can be used to make conventional aqueous solutions containing about 50 wt. % water, for use in known commercial processes for the manufacture of polyamide polymers.

The present invention also relates to a diamine/dicarboxylic acid salt obtainable by the process according to invention, or any embodiment thereof as described above. Preferably, the said according to the invention is an anhydrous salt, which comprises less than 0.5 wt. % water, relative to the total weight of the salt.

The salt obtained by the process according to the invention is free flowing, or substantially so. i.e at least easy flowing.

The flowability of powder material can be measured by different methods. A suitable method is the sheartest method according to ASTM D6773. This test can be performed with a Schulze Ringshear Tester. In this test the flowability is defined by the ratio (ffc) of consolidation stress, σ1, to unconfined yield strength, σc, For an easy flowing material the ffc should be above 4, more particular in the range between 4 and 10. For a free flowing material the ffc should be at least 10. According to Schulze a material with an ffc of 4 or less is too cohesive for proper flowability.

In the method applied herein further below the flowability was measured by the sheartest method according to ASTM D6773, with a Schulze Ringshear Tester, with a consolidation stress of 3 kPa, at 20° C., after a storage time of 10 minutes. The anhydrous diamine/dicarboxylic acid salt according to the invention has a flowability (ffc) of at more than 4, preferably more than 7, and even more preferred above 10.

It has been observed that the diamine/dicarboxylic acid salts obtained by the process according to invention have a particular morphology, which can be observed by microscopic techniques, more particular by scanning electron microscopy (SEM). The said diamine/dicarboxylic acid salt is a granulate material consisting of polycrystalline granules, the individual granules consisting of multiple micro-crystallites and/or micro-crystalline domains. The micro-crystallites are visible all over the surface of the granules. The micro-crystallites have a relatively narrow particle size distribution. The granules consist of such micro-crystallites or micro-crystalline domains throughout the granules, as can be observed from SEM pictures taken upon cutting the granules. The average size of the micro-crystallites inside the granules was observed to be smaller than of those on the surface.

The micro-crystallites typically have a small particle size, much smaller than the granules. Even the smallest granules appear to consist of multiple micro-crystallites.

Suitably, the granules consist of micro-crystallites having a diameter based particle size distribution, with a d90 of at most 2.5 μm. This means that at least 90% of the total number of micro-crystallites have a mean diameter of at most 2.5 μm.

Also suitably, the granules consist of micro-crystallites having a volume based particle size distribution, with a d90 of at most 5 μm. This means that at least 90% of the total volume of the micro-crystallites is made up of micro-crystallites having a mean diameter of at most 5 μm.

Herein the diameter is the mean diameter for individual micro-crystallites measured by software supported image analysis of SEM images taken from surface areas of granules, as described herein further below. The software used is "Analysis.auto", version 5.0, from the company Olympus America Inc. Based thereupon the diameter based particle size distribution and volume based particle size distribution are analysed.

For a representative and reliable measurement of the micro-crystalline domain size, the mean diameters of individual micro-crystallites, and the analysis of the diameter based particle size distribution and volume based particle size distribution, images from minimum three different granules should be analysed, for each granule a representative surface area should be selected, and the analysis per granules should comprise at least 75 individual particles on average. The results of the different particles can be combined in one list to allow for the calculation of a single overall particle size distribution.

In particular cases, the polycrystalline granules, or at least a large part thereof, in particular the larger granules, have a globular shape. With the term "globular shape" is herein understood a shape with rounded off edges without plane surfaces and crystallographic angles. Such shape can be more or less spherical, or a shape like a patoto or a wallnut, or alike. Several granules, in particular the larger ones, also show cracks, as in dried mud. Smaller particles typically have a less globular shape and more pronounced cracks.

In other cases, the percentage of granules with a globular shape is much less. In that case, even many of the bigger particles have a less globular shape and show very pronounced cracks. Also in these cases, all the granules consist of multiple micro-crystallites having a particle size much smaller than the granules.

The morphology with more globalur shapes is more observed with smaller diamines whereas the morphology with the more pronounced cracking is observed with larger diamines. Likewise this can be explained by a mechanism involving swelling of the dicarboxylic acid particles upon absorption and reaction with diamine, causing the particles to crack. This swelling, and thus the cracking will be more pronounced with larger diamines.

Where the micro-crystallites have a small particle size, the granules typically have a much larger particle size, even for the majority of the smaller granules.

Suitably, the salt granulate material have a particle size distribution, with a d10 of at least 20 µm. Also suitably, the granulate material has a particle size distribution with a a d90 of at most 1000 µm, and optionally also median particle size (d50) in the range of 50-600 µm, Herein the particle size distribution is measured by the method according to ISO 13320 as mentioned herein above.

In a preferred embodiment of the diamine/dicarboxylic acid salt the d10 is in the range of 20-200 µm, and/or the d50 is in the range of 50-500 µm, and/or d90 is in the range of 200-1000 µm. More particular, the d10 of the diamine/dicarboxylic acid salt granules is in the range of 20-200 µm, the d50 is in the range of 50-500 µm, and d90 is in the range of 200-1000 µm.

Also preferably, the polycrystalline granules have a particle size distribution with a Span, defined by the ratio of (d84-d16)/d50, of at most 5, preferably at most 2.5. The advantage is a more homogenous product, less fines and a better flowability.

A further characteristic of the diamine/dicarboxylic acid salt obtainable by the process according to the invention is that the granulate material generally has a low compressibility. The compressibility is determined by the comparing the aerated bulk density (ABD) and the tapped bulk density (TBD). Suitably, the compressibility, expressed by the ratio of (TBD-ABD)/TBD*100%, is at most 35%, wherein ABD is the aerated bulk density and TBD is the tapped bulk density both measured by the method according to ASTM D6393.

The salt according to the invention is suitably comprises the salt of one or of the dicarboxylic acids and one or more of the diamines, and any preferred combination thereof, as described herein further above.

Some examples include the following combinations: 6T/66; molar ratio suitably in the range of 80/20-20/80, for example 62/38; PA 6T/610; molar ratio suitably in the range of 90/10-30/70, for example 70/30; PA 6T/4T; molar ratio suitably in the range of 90/10-10/90, for example 60/40; and PA 6T/10T; molar ratio suitably in the range of 90/10-30/70, for example 70/30. Herein is 4T the salt based on 1,4-butane diamine and terephthalic acid. 6T is the salt based on 1,6-hexane diamine and terephthalic acid. 66 is the salt based on 1,6-hexane diamine and adipic acid. 610 is the salt based on1,6-hexane diamine and adipic acid. 10T is the salt based on 1,10-decane diamine and terephthalic acid.

More preferably, the salt comprises a salt based on 1,4-butane diamine and terephthalic acid and/or a salt based on 1,6-hexane diamine and terephthalic acid. More particular the is based on 1,4-butane diamine and terephthalic acid with terephthalic present in an amount of at least 70 mol % of total diacid and 1,4-butane diamine present in an amount of at least 10 mol % of total diamines. Even more preferably, the salt is an anhydrous 4T or 6T salt.

The invention also relates to the use of the salts in a polymerization process for the preparation of a polyamide.

The invention is further illustrated with the following examples and comparative experiments.

Methods

Melting Temperature.

The melting temperature (Tm) was measured by DSC according to the method of ISO11357-3.2, 2009, in an N2 atmosphere with heating and cooling rates of 20° C./min. Herein Tm was the temperature measured for the peak value of the melting peak in the first heating cycle.

Aerated Bulk Density (ABD) and Tagged Bulk Density (TBD)

The ABD and TBD were measured by the method according to ASTM D6393-08 ("Standard Test Method for Bulk Solids Characterization by Carr Indices", ASTM International, West Conshocken, Pa., DOI: 10.1520/D6393-08) with a Hosokawa Powder Tester at 20° C.

Particle Size Distribution

The particle size distribution of granulate material was measured by laser granulometry according to ISO 13320-1 with a Sympatec Helos (H0024) & Rodos apparatus at 20° C. with an applied pressure of 0.5 bar and an measured under-pressure in the venturi of 25 mbar.

Shear Test

The flowability was measured by the method according to ASTM Standard D6773-08 ("Standard Shear Test Method for Bulk Solids Using the Schulze Ring Shear Tester", ASTM International, West Conshocken, Pa., DOI: 10.1520/D6773-08). The shear test was performed with a Schulze Ringshear Tester at 20° C. with a consolidation stress of 3 kPa. The measurement was started immediately after filling of the tester.

Porosimetry

The porosity was measured by the method of Mercury Intrusion Porosimetry (MIP) experiments carried out on a Micromeritics Autopore IV 9505 porosimeter (www.micromeritics.com) in the pressure range from vacuum up to 22 MPa. Prior to the measurements, the samples were kept in vacuum for 16 h. The samples, about 0.15 g of dried material each, were then transferred and weighed in the sample holder.

Micro-Crystalline Domain Size

The size of the micro-crystalline domains was analysed with the help of the image analysis software program "Analysis.auto", version 5.0, from the company Olympus America Inc. For the analysis, SEM images taken from surface areas of different granules were used. Depending on the surface area of the granules covered by the image and the size of the micro-cystallites, selections of parts of the images were used.

In a typical example, the original image had a size corresponding with a surface area of 15×20 µm. The image had 3872×3306 pixels. From the image a representative part corresponding with a surface area of about 5×6 µm was selected. The image had 1238×963 pixels.

After selection of an appropriate part, the "Operation" procedure provided in the software program was performed as follows: first a shading correction was applied using N×N average filter with 6 iterations and size selection 6, as provided by the software. Then, the image is converted to a negative image. From the converted image a representative part was selected.

In the typical example the selection was about 3.4×4.0 µm (3.39×3.94 µm).

The selection was transformed into a binary image while applying a low value (equal or close to 0) for the low threshold and a high value (around 210) for the high thresholds for the detection set. In the binary image, contours are applied and corrected with the "edit image" option in the software to remove artefacts. This edited image is used for the "Particle analysis" procedure.

In this analysis, particles with a size of at least 10 pixels are detected. The detected particles are then analysed for the surface area, the smallest- and largest diameter and mean diameter. The resulting data are transferred to Excel.

For the further analysis as used herein the data for the mean diameters of the individual particles was used. Based on the values of the mean diameter of the individual particles a theoretical volume for each of the particles was calculated, assuming the particles being ideally spherical. Based thereupon, and combing the results of 3 different particles, a volume based particle size distribution was calculated and the d10, d50 and d90 values calculated.

Starting Materials

Terephthalic acid Industrial grade (BP Amoco); 0.05 wt. % water
Adipic acid Industrial grade (Rhodia); 0.09 wt. % water
Sebacic acid Industrial grade (Sigma Aldrich)); <0.1 wt. % water
1,4-butane diamine Industrial grade (DSM); <0.5 wt. % water
1,6-hexane diamine Industrial grade (Sigma Aldrich); <0.5 wt. % water
1,10-decane diamine Industrial grade (Sigma Aldrich); <0.5 wt. % water
In performing g to mol conversion, chemicals are seen as 100% pure.

SALT PREPARATION EXPERIMENTS

Example I

A mixture of 75 g of terephthalic acid and 40.4 g of adipic acid (62/38 mol %) was charged into a 1.0 liter baffled flask, attached to a rotary evaporator, equipped with a heated diamine dosing vessel was kept under an inert nitrogen atmosphere and mixed by rotation at 50 rpm. The rotating flask was partially submerged in a water bath, maintained at 60° C. to remove the heat of neutralization. Liquid 1,6-hexane diamine (86.6, i.e. around 2 molar % in excess of stoichiometric quantity, or D/DA=1.02) of 60° C. was added drop-wise to the acids in 4 hours under constant rotation. After dosing, the reaction mixture was stirred by rotation at a water batch temperature of 60° C. for another 20 minutes. After the experiment, salt in the form of loose powder, was obtained.

In similar manners as above, the compositions of Examples II-VI and listed in table 1 were prepared.

Example II

Example II was prepared as described in example I, starting from a mix of 79.3 g terephthalic acid and 41.4 g of sebacic acid (70/30 mol %) and adding 81.3 g of liquid 1,6-hexane diamine in 4 hours, resulting in a loose powder with D/DA=1.026

Example III

Example III was prepared as described in example I, starting from 122.5 g terephthalic acid and adding a liquid mix of 52.8 g 1,6-hexane diamine and 28.7 g 1,4-butane diamine (60/40 mol % excluding the 2.7 g 1,4-butane diamine excess) in 2 hours, resulting in a loose powder with D/DA=1.026.

Example IV

Example IV was prepared as described in example I, starting from 111.1 g terephthalic acid and adding a liquid mix of 56.4 g 1,6-hexane diamine and 34.6 g 1,10-decane diamine (62/38 mol % excluding the 2.0 g 1,6-hexane diamine excess) in 4 hours, resulting in a loose powder with D/DA=1.026.

Example V

Example V was prepared as described in example I, starting from 111.1 g terephthalic acid and adding 84.3 g liquid 1,6-hexane diamine in 5 hours, resulting in a loose powder with D/DA=1.024.

Example VI

Example VI was prepared as described in example I, using a 2 liter baffled flask starting from 326.65 g terephthalic acid and adding 178.35 g liquid 1,4-butane diamine in 3 hours, resulting in a loose powder with D/DA=1.029.

Comparative Experiment A: 4T Salt Preparation in Water Via an Aqueous Solution Process A 2000 ml three necked flask, equipped with a reflux condenser, a temperature sensor and a magnetic stirring rod was charged with 300 g demineralized water and 104.01 g DAB. Over 1 minute 195.99 g terephthalic acid (TPA) is added via a funnel attached to the third neck. In course of the TPA addition, the 4T salt forms as a white slurry. 600 g water was added and subsequently, the reaction mixture was heated to T=90° C. at which temperature the 4T salt was dissolved. The product was then cooled in a water/ice bath and the cooled slurry was filtered over a Büchner funnel. The mother liquor was mixed with 800 ml ethanol and the precipitated salt collected on the same Büchner funnel. The filter cake was washed with 200 ml ethanol. After air drying, by allowing a stream of air to pass through the filter cake for 16 hours, the product was mixed to homogenize the two precipitation fractions and dried under vacuum (50 mbar abs Pressure) at 40° C. for by for 3 hours. The product had a melting point of 283° C., determined by DSC.

TABLE 1

Salt preparation results, laboratory scale

| | Salt Composition | Molar ratio | Observations | Tm (° C.) |
|---|---|---|---|---|
| Example I | 6T/66 | 62/38 | powder obtained | 199, 275 |
| Example II | 6T/610 | 70/30 | powder obtained | 180, 277 |
| Example III | 6T/4T | 60/40 | powder obtained | 280 |
| Example IV | 6T/10T | 70/30 | powder obtained | 254, 264 |
| Example V | 6T | | powder obtained | 280 |
| Example VI | 4T | | powder obtained | 283 |
| Comp. Ex. A | 4T | | Powder | 283 | a) In case of using more than two diamines, for calculating the molar composition of the copolyamides, the diamine excess was accounted to the lowest molar mass diamine in the diamine mix and was not included for the molar ratio composition calculation.

Table 2 shows an overview of properties measured for 4T salt of Example VI and 4T salt of Comparative experiment A (CE-A). Microscopic pictures of these materials are shown in the attached figures.

TABLE 2

Properties of 4T salt of Example VI and 4T salt of Comparative experiment A

| | EX-VI | CE-A |
|---|---|---|
| Particle Size Distribution | | |
| d10 (µm) | 45 | 4.6 |
| d50 (µm) | 143 | 42 |
| d90 (µm) | 292 | 503 |
| d16 (µm) | 60 | 7.0 |
| d84 (µm) | 253 | 370 |

TABLE 2-continued

Properties of 4T salt of Example VI and 4T salt of Comparative experiment A

| | EX-VI | CE-A |
|---|---|---|
| d99 (μm) | 441 | 796 |
| Span ((d84 − d16)/d50) | 1.35 | 8.33 |
| Sheartest | | |
| Sigma 1 [Pa] | 5731 | 6103 |
| FC [Pa] | 4 | 1878 |
| FFC [—] | 1500 | 3 |
| Phie [°] | 37 | 40 |
| Aerated Bulk Density (ABD) and Tapped Bulk Density (TBD) | | |
| ABD [kg/m3] | 523 | 360 |
| TBD [kg/m3] | 675 | 625 |
| Compressibility (1 − (ABD/TBD)) | 0.225 | 0.424 |
| Mercury Porosimetry | | |
| Peak (μm) | 70 | 10 |
| Peak hight (dV/dlogD) (cm³/g) | 2.25 | 1.3 |
| Above 100 μm | Little | Significant |
| Porosity (%) | 53 | 59 |

The results not only show differences in particle size distribution and flow behaviour, but also in the crystalline morphology. EX-VI shows a narrow particle size distribution with a relatively high d10 and low span, and a low compressibility, whereas CE-A shows a broader particle size distribution with a lower d10 and higher span, and a higher compressibility. The difference in particle size distribution and compressibility is also reflected in the porosity measurements. Most of the porosity is found in "pores" with a pore size in the range of 5-500 μm (EX-VI), respectively 2-600 μm (CE-A), likewise corresponding with the inter-particle porosity. EX-VI has a peak at larger pore size (70 μm), which is higher and more narrow (running from 20-100 μm) than that of CE-A. CE-A has a lower, but much broader pore size distribution, with the peak at much lower pore size (10 μm), but still with a significant amount of pores with a size above 100 μm.

The different crystalline morphologies are further illustrated with the SEM-images shown in FIGS. 1-5.

FIG. 1: SEM image of 4T salt from Comparative Example A.

FIG. 2-5: SEM images of 4T salt from Example VI.

FIG. 1 shows a SEM image taken of 4T salt from Comparative Example A. The image shows large irregular shaped granules composed of multiple smaller crystals with relative large size, respectively composed of a limited number of crystals with a even larger size and rather flat surface areas. Next to that these larger granules, there are visible a large number of small granule, several consisting of a single crystal or only a few crystals. Many of these crystals are still in the size range around 5-10 μm.

FIG. 2 shows an SEM image taken of 4T salt from Example VI. The image shows a large number of granules with a globular shape. The smaller particles have a less globular shape. The number of small particles is relatively low.

Micro-Crystalline Domain Size of Example VI

For the salt of Example VI the particle size distribution of the micro-crystalline domains was determined both on the surface on the particles, and inside the particles. For the latter cross-cut particles were used. FIGS. 6-14 illustrate the different steps in the analytical procedure, starting with a SEM image of the inside of a salt granule (FIG. 6), respectively with a SEM image of the inside of a salt granule (FIG. 10), of example VI. Results are presented in table 3.

FIG. 6-9: Images of microcrystalline domains inside a 4T granule, following different steps in the particle size analysis.

FIG. 10-13: Images of microcrystalline domains on the outside of a 4T granule, following different steps in the particle size analysis.

Figure 1:
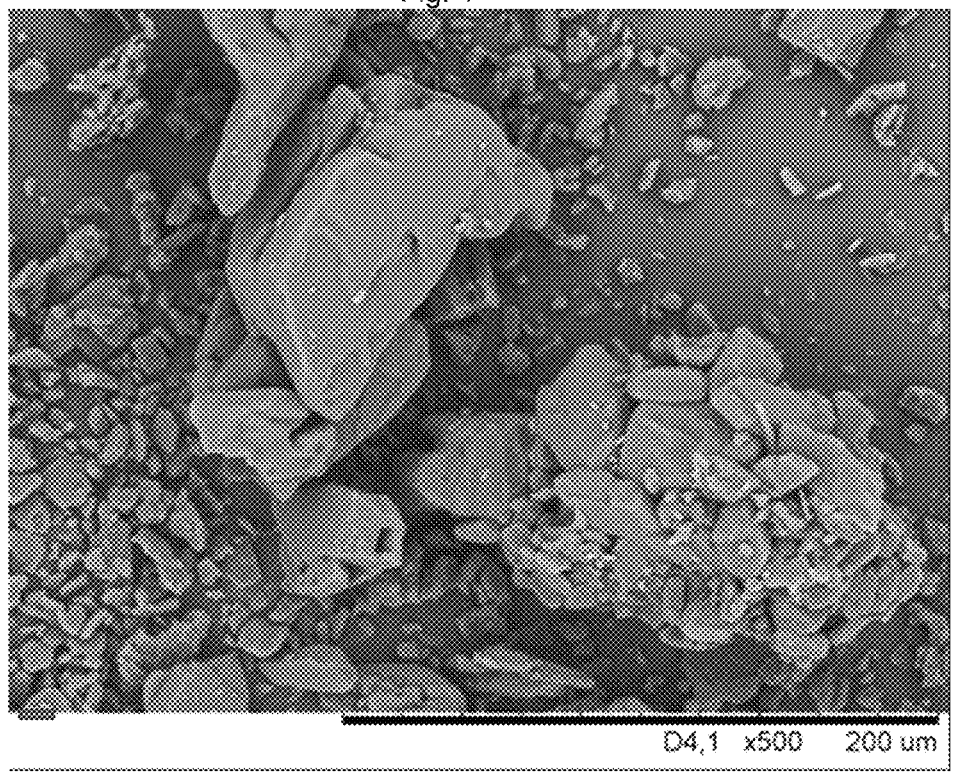
Figure 2:
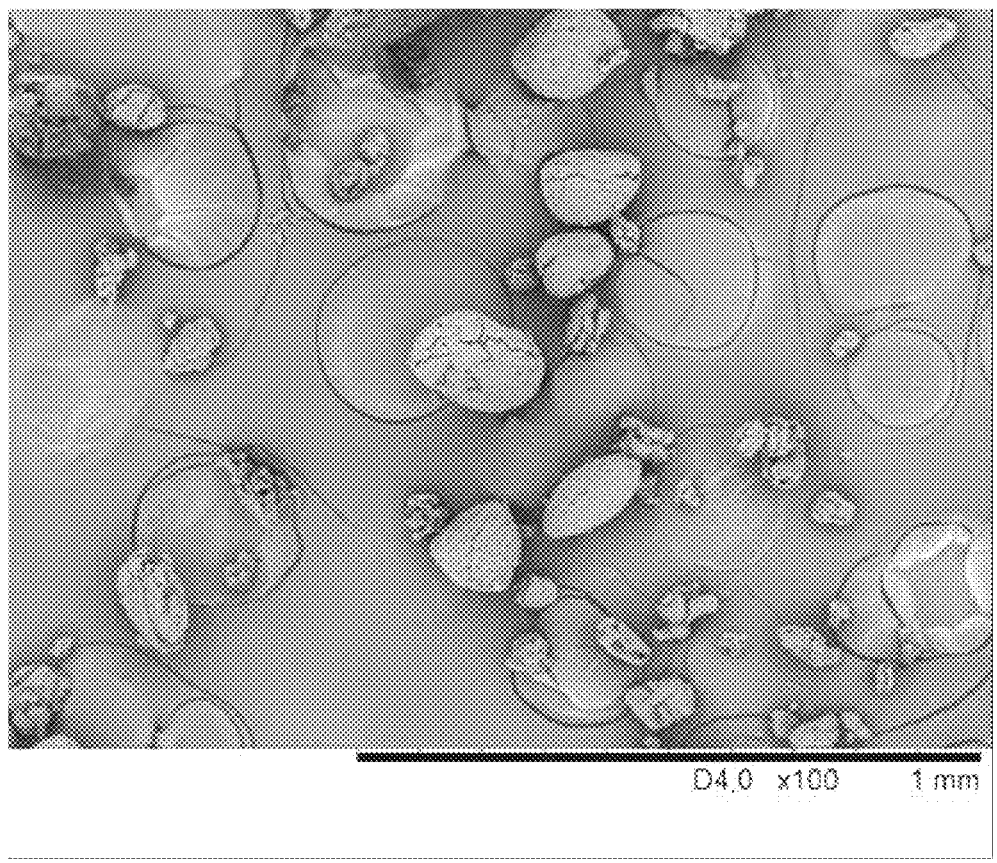
Figure 3:
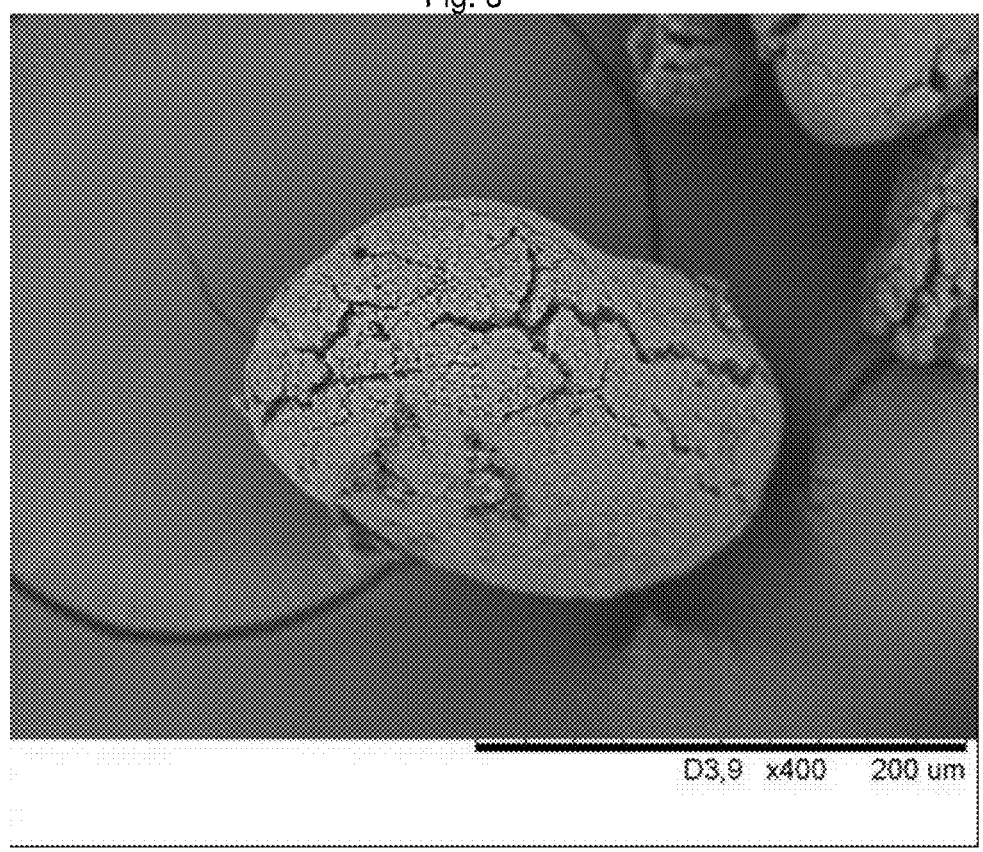
FIG. 3 shows an SEM image taken from a selected area of the SEM image of FIG. 2, highlighting a granule with a globular shape. In the granule effects of cracking, like in dried mud, are visible.
Figure 4:
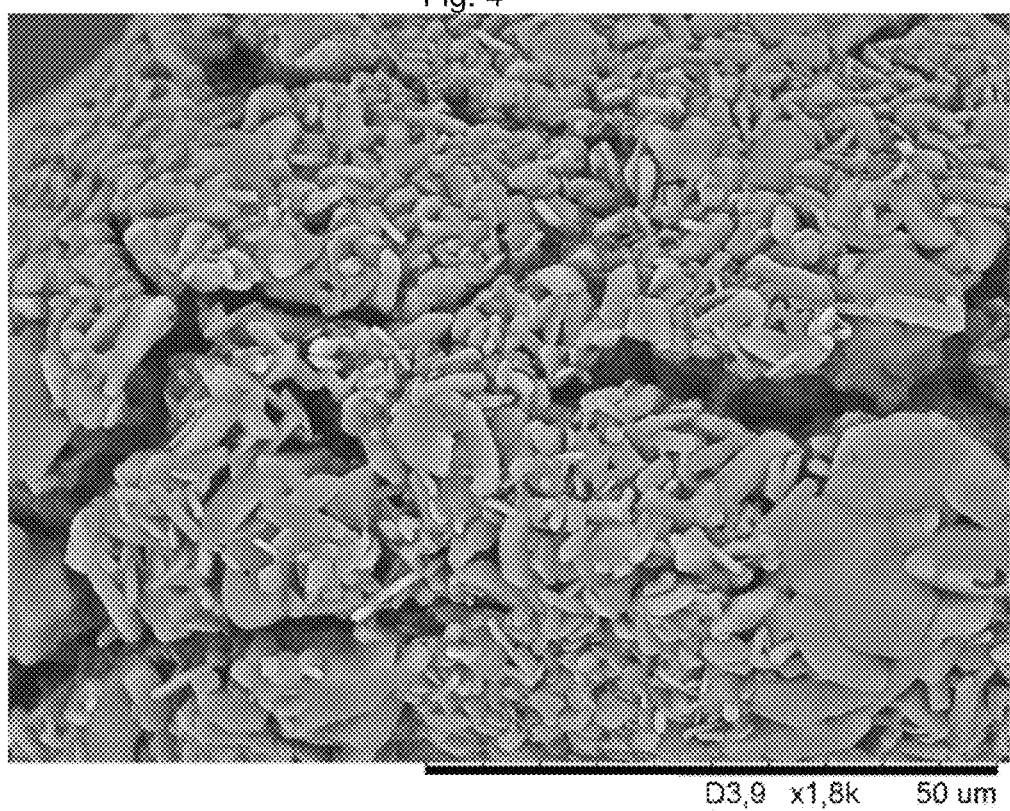
FIG. 4 shows an SEM image taken from a selected area of the SEM image of FIG. 3, highlighting the surface area of the globular granule. On the surface of the granule, many small crystallites are visible.
Figure 5:
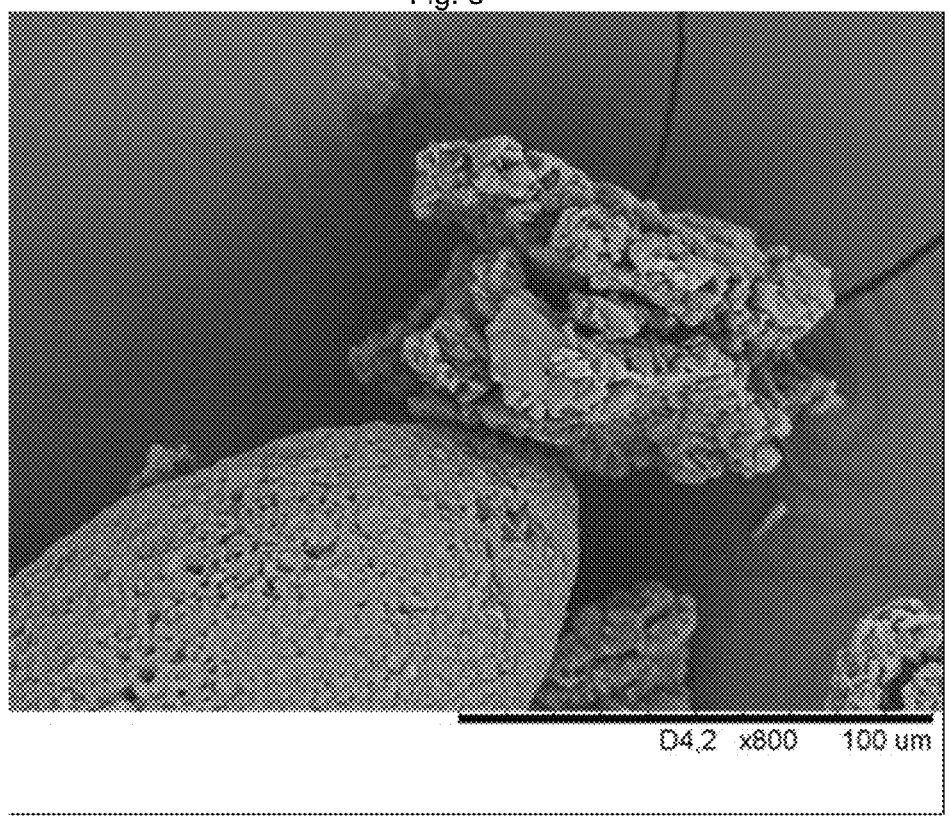
FIG. 5 shows an SEM image taken from another selected area of the SEM image of FIG. 2, highlighting a part of a granule with a globular shape and a smaller granule with a more irregular shape. The latter granule shows even more severe effects of cracking, like in dried mud, compared to the globular granule of FIG. 3.
Figure 6:
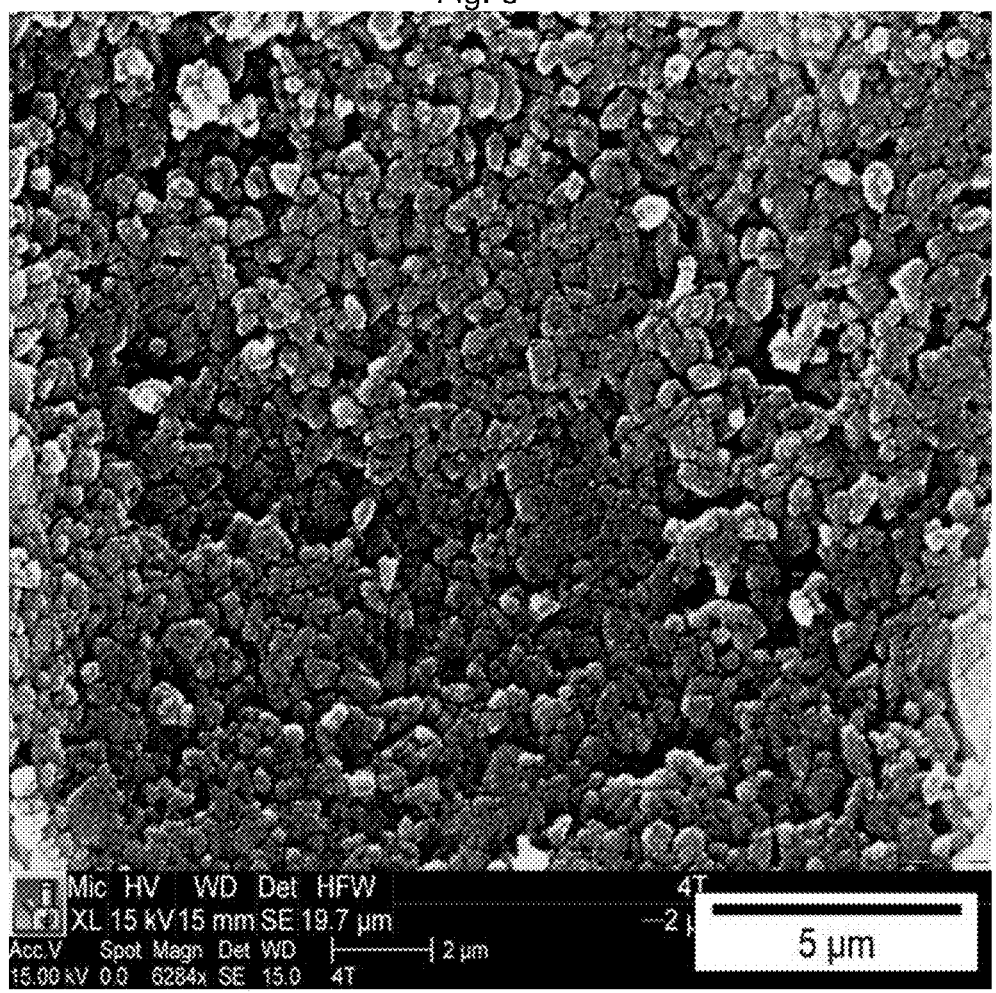

FIG. 6 shows the original SEM image of the 4T salt of example VI, showing the microcrystalline domains inside a granule.

Figure 7:
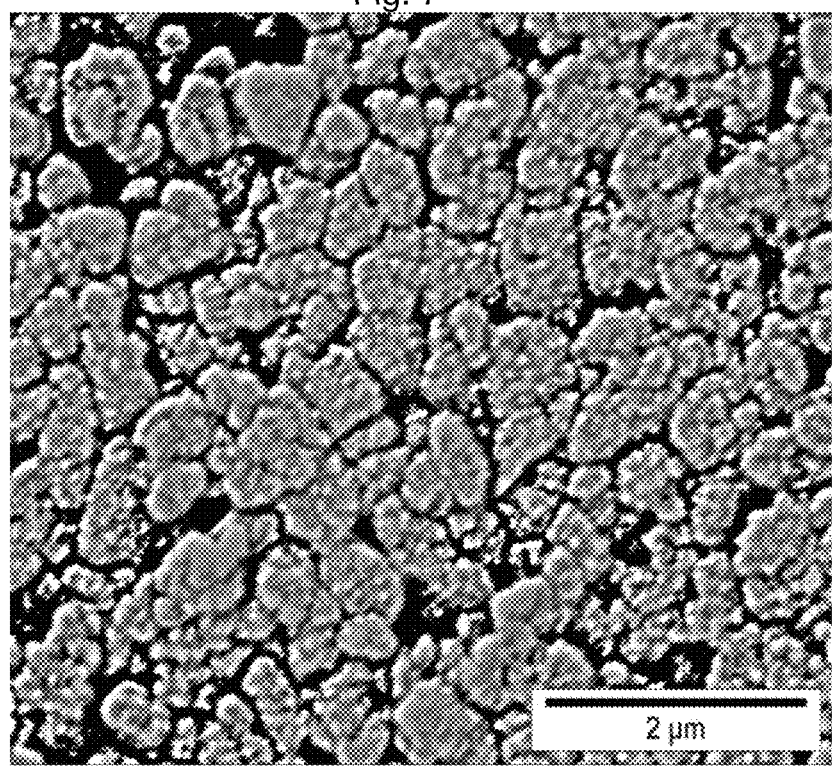

FIG. 7 shows a selection of FIG. 6, wherein the image has been optimized in contrast and shading correction has been applied.

Figure 8:
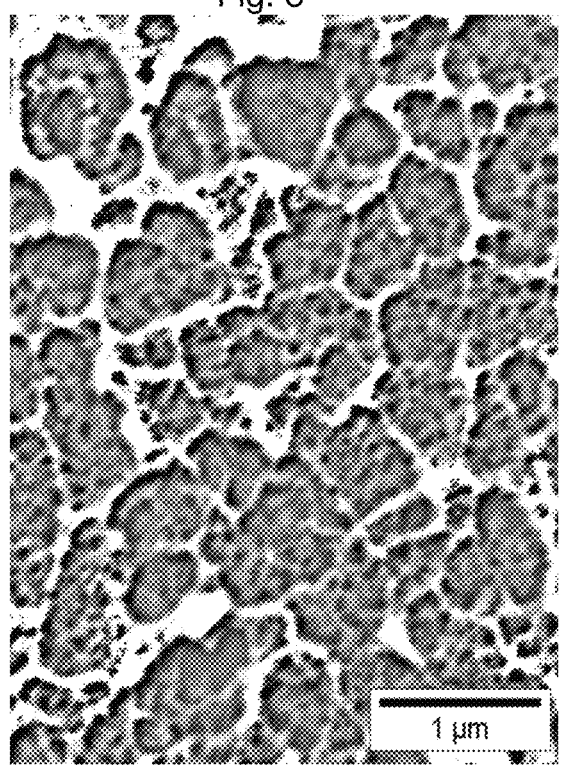

FIG. 8 shows a selection of FIG. 7, wherein the image has been inverted and further optimized in contrast.

Figure 9:
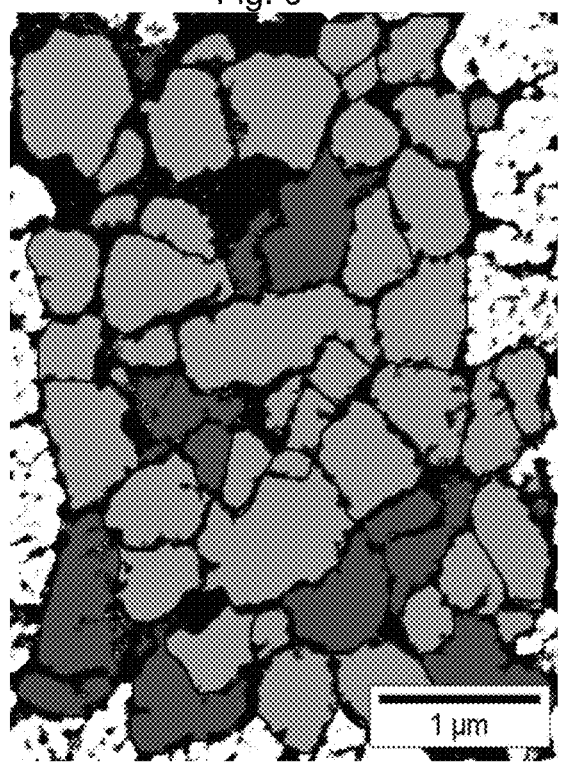

FIG. 9 shows a selection of FIG. 8, wherein the image has been binarized, edited and made ready for the particle size analysis.

Figure 10:
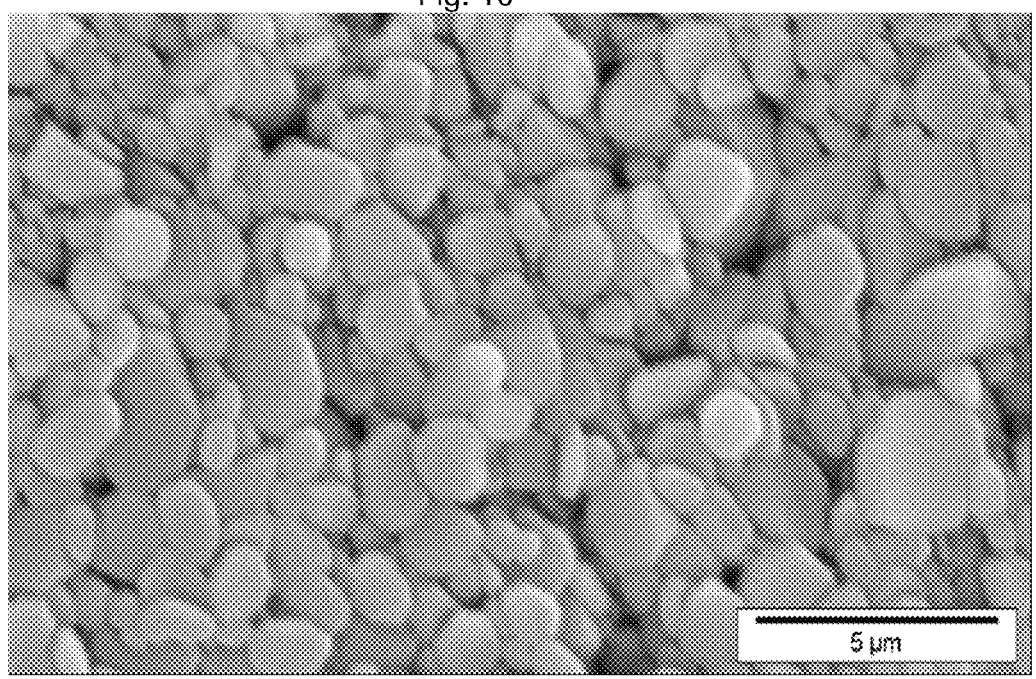

FIG. 10 shows a SEM image of the 4T salt of example VI, showing the microcrystalline domains on the outside of a granule. The SEM image is already optimized in contrast and shading correction has been applied.

Figure 11:
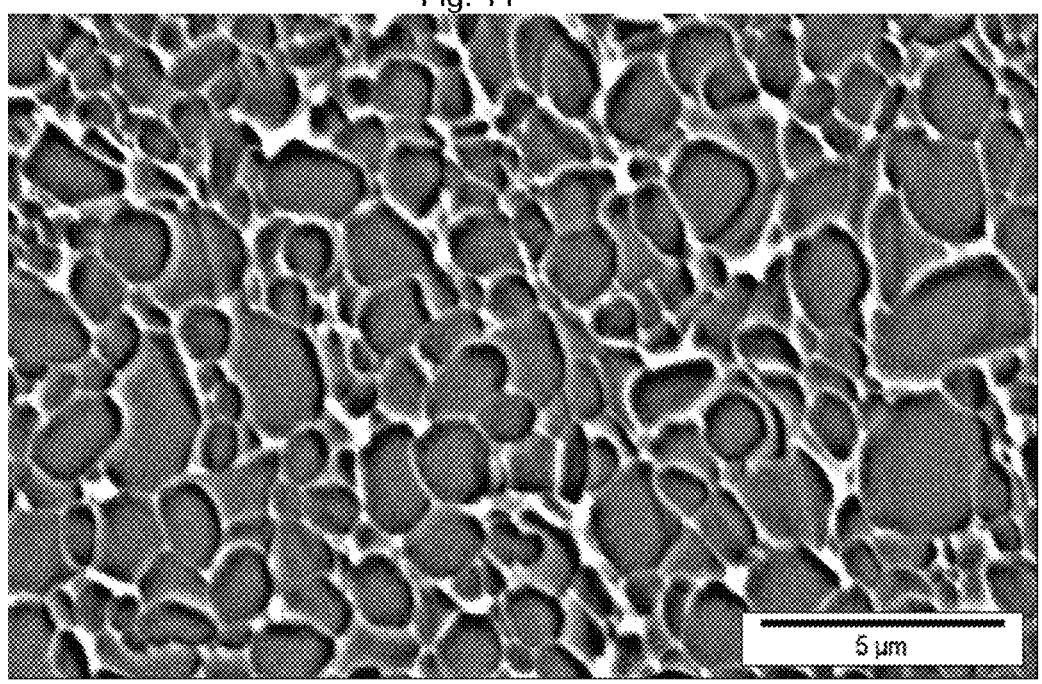

FIG. 11 shows a selection of FIG. 10, wherein the image has been inverted and further optimized in contrast.

Figure 12:
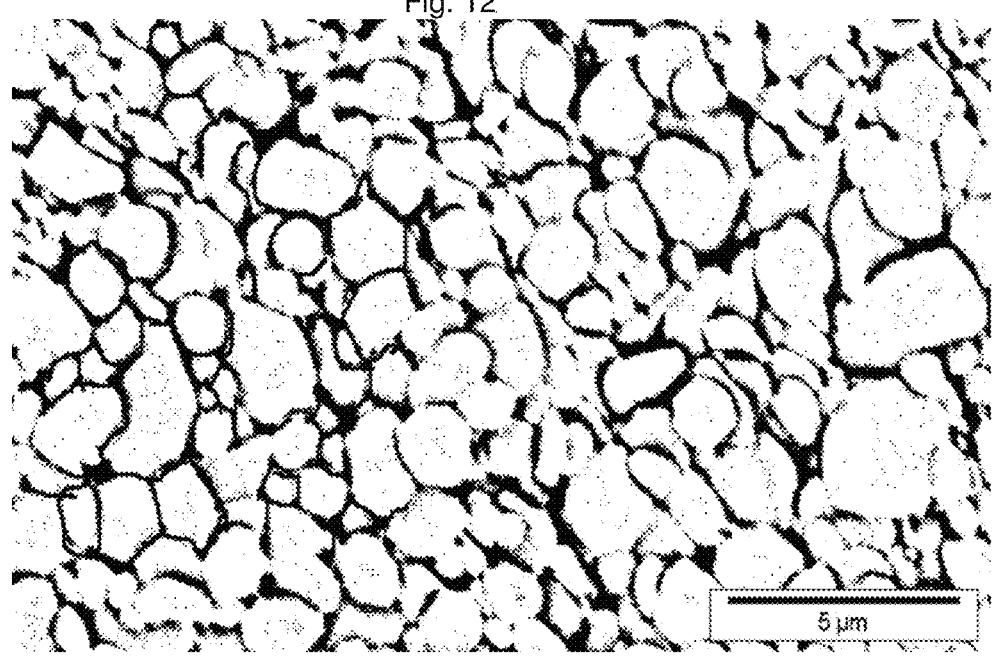

FIG. 12 shows a the same selection as of FIG. 8, wherein the image has been binarized.

FIG. 13 shows a selection of FIG. 12, wherein the image has been edited and made ready for the particle size analysis.

TABLE 3

Results of the micro-crystalline domain size analysis of Example VI

| Particle size | Inside | Outside |
|---|---|---|
| D10-volume based (nm) | 469 | 1080 |
| D50-volume based (nm) | 724 | 1880 |
| D90-volume based (nm) | 1050 | 2350 |
| Smallest (nm) | 12 | 140 |
| Largest (nm) | 1128 | 2700 |
| D50-diameter based (nm) | Around 300 | Around 1100 |

Examples VII and VIII

Examples VII and VIII were repetitions of Example VI, except that the terephthalic acid used was different. For Example VII a special grade with a narrow particle size distribution and a small median particle size was used. For Example VIII a special grade also with a narrow particle size distribution but with a larger median particle size was used. In both cases a free flowing powder was obtained. The results for the particle size distribution for the specific grades of terephthalic acid (referred to as Comparative experiment B and C) and Example VII and Example VIII and the flowability of 4T salt of Example VII and Example VIII are shown in Table 4.

TABLE 4

Properties of 4T salt of Example VII and Example VIII and terephthalic acid of Comparative Experiment B and C.

|  | CE-TPA | EX-VII 4T | CE-TPA | EX-VIII 4T |
|---|---|---|---|---|
| Particle Size Distribution |  |  |  |  |
| D10 | 30 | 44 | 110 | 100 |
| D50 | 81 | 107 | 200 | 240 |
| d90 | 141 | 177 | 321 | 365 |
| d16 | 39 | 56 | 133 | 155 |
| d84 | 126 | 163 | 288 | 338 |
| d99 | 196 | 263 | 490 | 502 |
| Span ((d84 − d16)/d50) | 1.07 | 1.00 | 0.78 | 0.76 |
| Sheartest |  |  |  |  |
| Sigma 1 [Pa] |  | 5848 |  | 6152 |
| FC [Pa] |  | 304 |  | 528 |
| FFC [—] |  | 19 |  | 12 |
| Phie [°] |  | 37 |  | 39 |
| Aerated Bulk Density (ABD) and Tapped Bulk Density (TBD) |  |  |  |  |
| ABD [kg/m3] | 846 | 548 | 884 | 489 |
| TBD [kg/m3] | 1064 | 678 | 1026 | 594 |
| Compressibility (1 − (ABD/TBD)) | 0.205 | 0.191 | 0.139 | 0.177 |

The results show that particle size distribution of the terephthalic acid starting material is directly reflected in the particle size distribution, apart from the fact that the dimensions, or at least most of them, have gone up systematically. This increase in particle size, in combination with retention of the particle size distribution, might be explained absorption and reaction of the diamine with the dicarboxylic acid, thereby expanding the dicarboxylic acid particles without breaking them up. At the same time the density has gone down significantly, most for EX VIII, but the compressibility is still very low. The lower density may be due to lower intrinsic density of the salt compared to the acid as well as due to small cracks in the particles and small spacing between micro-crystallites. The results of the shear test show that both materials are free flowing.

Example IX

Mixtures of adipic acid (ranging from 25 to 100 kg per batch) and terephthalic acid (ranging from 350 to 425 kg per batch) were charged into a 3000 liter tumble dryer. After inertization with nitrogen, a mixture of molten (100%, industrial grade) 1,4-butane diamine (25-100 kg) and 1,6-hexane diamine (200-275 kg) of 50° C. was sprayed onto the solid acids at atmospheric pressure, through a perforated plate distributer, in approx. 4 hours, while tumbling the complete dryer mass. The product temperature was measured in time using a PT-100 element inside the dryer and the dryer content was maintained below 80° C. by cooling via the dryer walls. After dosing and mixing for another hour, the salt obtained had the appearance of a free-flowing, crystalline, white powder.

Example X

Mixtures of adipic acid (ranging from 2.5 to 10 kg per batch) and terephthalic acid (ranging from 35 to 42.5 kg per batch) were charged into a 180 liter conical dryer with a helical stirrer. After inertization with nitrogen, first (100%, industrial grade) 1,4-butane diamine (2.5-10 kg), then (100%, industrial grade) 1,6-hexane diamine (20-27.5 kg) were sprayed onto the solid acids at atmospheric pressure, through a 4 pipe (Swazeloc ⅛") distributer, in approx. 1.5 to 2 hours, while agitating the reaction mass with the helical stirrer. The product temperature was measured in time using a PT-100 element flush with the dryer wall and the dryer content was maintained below 65° C. by cooling via the dryer walls. After dosing, heating to 150° C. under nitrogen and subsequent cooling, the salt obtained had the appearance of a free-flowing, crystalline, white powder. The same procedure was repeated several times using pre-mixed amine mixtures of 1,4-butane diamine (2.5-10 kg) and (100%, industrial grade) 1,6-hexane diamine (20-27.5 kg), leading to very similar, free-flowing, crystalline, white powders.

Example XI

Terephthalic acid (45 kg) was charged into a 180 liter conical dryer with a helical stirrer. After inertization with nitrogen, a mixture of (100%, industrial grade) 1,4-butane diamine (2.5-10 kg) and (100%, industrial grade) 1,6-hexane diamine (20-27.5 kg) was sprayed onto the solid acid at atmospheric pressure, through a 4 pipe (Swazeloc ⅛") distributer, in approx. 1.5 to 2 hours, while agitating the reaction mass with the helical stirrer. The product temperature was measured in time using a PT-100 element flush with the dryer wall and the dryer content was maintained below 65° C. by cooling via the dryer wall. After dosing, and mixing for another hour, the salt obtained had the appearance of a free-flowing, crystalline, white powder.

Example XII

Mixtures of adipic acid (ranging from 0.6 to 2.7 kg per batch) and terephthalic acid (ranging from 9.3-11.3 kg per batch) were charged into a 50 liter DRAIS ploughshare mixer. After inertization with nitrogen, a mixture of (100%, industrial grade) 1,4-butane diamine (0.6-2.7 kg) and (100%, industrial grade) 1,6-hexane diamine (5.4-7.4 kg) was sprayed onto the solid acids at atmospheric pressure, through a single (Swazeloc ⅛") pipe, in around 1 hour, while agitating the reaction mass with the ploughshare mixer. The product temperature was measured in time using a PT-100 element inserted into the dryer in between the ploughshares, and the dryer content was maintained below 70° C. by cooling via the mixer. After dosing and mixing for another hour, the salt obtained had the appearance of a free-flowing, crystalline, white powder.

Example XIII

Mixtures of adipic acid (ranging from 0.8 to 3.3 kg per batch), terephthalic acid (ranging from 11.6 to 14.2 kg per batch) and benzoic acid (ranging from 0.1 to 0.6 kg per batch) were charged into a 100 liter tumble dryer. After inertization with nitrogen, a mixture of molten (100%, industrial grade) 1,4-butane diamine (0.8-3.3 kg) and 1,6-hexane diamine (6.6-9.2 kg), at a temperature of 50° C., was sprayed onto the solid acids at atmospheric pressure, through a 4 fold (Swazeloc ⅛") pipe distributer, in approx. 2 hours, while tumbling the complete dryer mass. The product temperature was measured in time using a PT-100 element inside the dryer and the dryer content was maintained below 80° C. by cooling via the dryer walls. After dosing and mixing for another hour, the salt obtained had the appearance of a free-flowing, crystalline, white powder.

The invention claimed is:
1. A process for preparing a diamine/dicarboxylic acid salt comprising the steps of:
   (i) forming a reaction mixture by contacting a diamine liquid with a dicarboxylic acid powder comprising an aromatic dicarboxylic acid, wherein the dicarboxylic acid powder has a particle size distribution with a Span, defined by a ratio of (d84−d16)/d50, of at most 5; and
   (ii) allowing the diamine and the aromatic dicarboxylic acid in the reaction mixture to react to form a diamine/dicarboxylic acid salt, wherein
   step (i) comprises the steps of:
   (a) gradually dosing the diamine liquid to the aromatic dicarboxylic acid powder, while keeping the aromatic dicarboxylic acid powder in constant movement, and thereafter
   (b) keeping the reaction mixture in constant movement for a time period directly following completion of the dosing; wherein
   steps of (a) and (b) are carried out at a temperature above 0° C. and below all of the following: the boiling temperature of the diamine and the melting temperatures of the dicarboxylic acid, the diamine/dicarboxylic acid salt and any intermediate reaction product, and wherein
   the reaction mixture in steps (a) and (b) comprises at most 5 wt. % of water, relative to the total weight of the diamine and dicarboxylic acid; and wherein
   the diamine consists of a mixture of different diamines.
2. The process according to claim 1, wherein the diamine and the dicarboxylic acid in the reaction mixture are present in a molar ratio of diamine over dicarboxylic acid in the range of 0.9-1.1.
3. The process according to claim 1, wherein the dicarboxylic acid powder is a mixture of an aliphatic dicarboxylic acid and an aromatic dicarboxylic acid.
4. The process according to claim 3, wherein the mixture of aliphatic dicarboxylic acid and aromatic dicarboxylic acid is a dry blend of solid particles of the aliphatic dicarboxylic acid and solid particles of the aromatic dicarboxylic acid.
5. The process according to claim 3, wherein the aliphatic dicarboxylic acid and the aromatic dicarboxylic acid are present in a molar ratio between 90:10 and 10:90.
6. The process according to claim 1, wherein the dicarboxylic acid consists of 90-100 mole % of aromatic dicarboxylic acid and 10-0 mole % of aliphatic dicarboxylic acid.
7. The process according to claim 1, wherein the aromatic dicarboxylic acid comprises either isophthalic acid, terephthalic acid or naphthalene dicarboxylic acid, or any combination thereof.
8. The process according to claim 1, wherein the aliphatic dicarboxylic acid comprises adipic acid and/or sebacic acid.
9. The process according to claim 1, wherein the diamine comprises an aliphatic diamine having 4-12 carbon atoms.
10. The process according to claim 9, wherein the diamine comprises 1,4-butane diamine and/or 1,6-hexane diamine.
11. The process according to claim 1, wherein step (i) comprises contacting the diamine liquid and the dicarboxylic acid powder by spraying or dripping the diamine liquid onto dicarboxylic acid powder while moving the dicarboxylic acid powder.
12. The process according to claim 1, wherein step (i) comprises contacting and mixing the diamine liquid and the dicarboxylic acid powder in a tumble mixer, a ploughshare mixer, a conical mixer, a planetary screw mixer or a fluidized bed reactor.
13. The process according to claim 1, wherein step (i) comprises contacting the diamine liquid and the dicarboxylic acid powder at a temperature between 0° C. and the boiling temperature of water.
14. The process according to claim 1, which further comprises the step of (iii) removing neutralization heat produced upon reaction of the diamine and the dicarboxylic acid to form the diamine/dicarboxylic acid salt via a heat exchanger.
15. A diamine/dicarboxylic acid salt, derived from dicarboxylic acid comprising an aromatic dicarboxylic acid and diamine comprising of a mixture of different aliphatic diamines, wherein the salt is a granulate material obtained by the process according to claim 1.
16. The salt according to claim 15, wherein the salt is an anhydrous salt, comprising less than 0.5 wt. % water, relative to the total weight of the salt.
17. The salt according to claim 15, wherein the salt has a flowability defined by the ratio (ffc) of consolidation stress, σ1, to unconfined yield strength, ac, measured by the shear test method according to ASTM D6773 of at least 10.
18. The salt according to claim 15, wherein the salt is a granulate material consisting of polycrystalline granules comprising micro-crystallites, wherein the micro-crystallites have a particle size distribution, measured by software supported analysis of SEM images taken from surface areas of granules, with a volume based d90 of at most 5 μm.
19. The salt according to claim 15, wherein the salt is a granulate material consisting of polycrystalline granules, wherein the polycrystalline granules have a particle size distribution, measured by the method according to ISO 13320, with a d10 of at least 20 μm, a d90 of at most 1000 μm, and a median particle size (d50) in the range of 50-600 μm.
20. The salt according to claim 19, wherein the dl0 is in the range of 20-200 μm, the d50 is in the range of 50-500 μm, and the d90 is in the range of 200-1000 μm.
21. The salt according to claim 15, wherein the polycrystalline granules have a particle size distribution with a Span, defined by the ratio of (d84−d16)/d50, of at most 5.
22. The salt according to claim 15, wherein the granulate material has a compressibility, expressed by the ratio of (TBD−ABD)/TBD*100%, of at most 35%, wherein ABD is an aerated bulk density and TBD is a tapped bulk density both measured by the method according to ASTM D6393.
23. The salt according to claim 15, wherein the salt comprises a salt based on 1,4-butane diamine and terephthalic acid and/or a salt based on 1,6-hexane diamine and terephthalic acid.
24. The salt according to claim 21, wherein the Span of the polycrystalline granules is at most 2.5.
25. A process for the preparation of a polyamide which comprises forming a polyamide using the salt according to claim 15.

* * * * *